(12) United States Patent
Khajavi et al.

(10) Patent No.: US 10,888,355 B2
(45) Date of Patent: *Jan. 12, 2021

(54) PERCUTANEOUS PEDICLE SCREW REVISION SYSTEM

(71) Applicant: Spinal Elements, Inc., Carlsbad, CA (US)

(72) Inventors: Kaveh Khajavi, Atlanta, GA (US); David E. Lane, II, Atlanta, GA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,795

(22) Filed: Jul. 6, 2018

(65) Prior Publication Data

US 2018/0310963 A1    Nov. 1, 2018

Related U.S. Application Data

(62) Division of application No. 15/440,877, filed on Feb. 23, 2017, now Pat. No. 10,039,573, which is a division of application No. 14/341,358, filed on Jul. 25, 2014, now Pat. No. 9,610,104.

(60) Provisional application No. 61/858,431, filed on Jul. 25, 2013.

(51) Int. Cl.
| | |
|---|---|
| *A61B 17/00* | (2006.01) |
| *A61B 17/56* | (2006.01) |
| *A61B 17/70* | (2006.01) |
| *A61B 50/30* | (2016.01) |

(52) U.S. Cl.
CPC .... *A61B 17/7002* (2013.01); *A61B 17/00234* (2013.01); *A61B 17/7049* (2013.01); *A61B 50/30* (2016.02); *A61B 2017/564* (2013.01)

(58) Field of Classification Search
CPC .......... A61B 17/7002; A61B 17/00234; A61B 17/7049; A61B 17/7055; A61B 17/7071; A61B 17/7063; A61B 17/7053; A61B 2017/564; A61B 50/30
USPC ................................................ 606/246–279
See application file for complete search history.

(56) References Cited

U.S. PATENT DOCUMENTS

| | | |
|---|---|---|
| 5,885,286 A | 3/1999 | Sherman et al. |
| 6,224,598 B1 | 5/2001 | Jackson |
| 6,485,491 B1 | 11/2002 | Farris et al. |
| 6,676,661 B1 | 1/2004 | Martin Benlloch et al. |
| 7,163,538 B2 | 1/2007 | Altarac et al. |
| 7,204,838 B2 | 4/2007 | Jackson |
| 7,645,294 B2 | 1/2010 | Kalfas et al. |
| 7,666,210 B2 | 2/2010 | Franck |
| 7,691,145 B2 | 4/2010 | Reilley et al. |
| 7,717,939 B2 | 5/2010 | Ludwig et al. |
| 7,736,370 B2 * | 6/2010 | Sweeney ............ A61B 17/7052 600/210 |
| 7,833,251 B1 | 11/2010 | Ahlgren et al. |
| 7,896,902 B2 | 3/2011 | Jeon et al. |
| RE42,545 E | 7/2011 | Ralph et al. |
| 8,012,184 B2 | 9/2011 | Schlapfer et al. |
| 8,100,909 B2 | 1/2012 | Butler et al. |

(Continued)

*Primary Examiner* — Pedro Philogene

(57) ABSTRACT

The present invention describes a system, devices and methods for percutaneous pedicle screw revision procedures. The present invention utilizes a tulip rod stub/connector adapted to be used to extend pedicle screw/rod constructs with minimal disruption to surrounding soft tissue and without having to remove existing hardware.

10 Claims, 18 Drawing Sheets

(56) References Cited

U.S. PATENT DOCUMENTS

| | | |
|---|---|---|
| 8,197,512 B1 | 6/2012 | Hunt et al. |
| 8,337,532 B1 | 12/2012 | McClean |
| 8,758,411 B1 | 6/2014 | Rayon et al. |
| 8,852,241 B2 | 10/2014 | Dalta |
| 9,125,691 B2 | 9/2015 | Gunn |
| 9,603,634 B1 * | 3/2017 | Frankel ............... A61B 17/7049 |
| 9,610,104 B2 * | 4/2017 | Khajavi ............. A61B 17/7002 |
| 10,456,176 B2 * | 10/2019 | McLean ................. A61B 17/88 |
| 2003/0004512 A1 | 1/2003 | Farris et al. |
| 2003/0199873 A1 | 10/2003 | Richelsoph |
| 2004/0057789 A1 | 3/2004 | Vagn-Erik |
| 2004/0116928 A1 | 6/2004 | Young et al. |
| 2005/0107789 A1 | 5/2005 | Sweeney |
| 2005/0113831 A1 | 5/2005 | Franck |
| 2005/0240265 A1 | 10/2005 | Kuiper et al. |
| 2006/0064091 A1 | 3/2006 | Ludwig et al. |
| 2007/0073291 A1 | 3/2007 | Cordaro et al. |
| 2007/0233078 A1 | 10/2007 | Justis et al. |
| 2007/0250061 A1 | 10/2007 | Chin et al. |
| 2007/0270832 A1 | 11/2007 | Moore |
| 2007/0276374 A1 | 11/2007 | Broman et al. |
| 2008/0071274 A1 | 3/2008 | Ensign |
| 2008/0097441 A1 | 4/2008 | Hayes et al. |
| 2008/0119858 A1 | 5/2008 | Potash |
| 2008/0177318 A1 | 7/2008 | Veldman et al. |
| 2008/0221622 A1 | 9/2008 | Triplett et al. |
| 2008/0306513 A1 | 12/2008 | Winslow et al. |
| 2008/0306527 A1 | 12/2008 | Winslow et al. |
| 2008/0312692 A1 | 12/2008 | Brennan et al. |
| 2009/0024169 A1 | 1/2009 | Triplett et al. |
| 2009/0030463 A1 | 1/2009 | Samudrala et al. |
| 2009/0036934 A1 | 2/2009 | Biedermann et al. |
| 2009/0069852 A1 | 3/2009 | Farris et al. |
| 2009/0105760 A1 | 4/2009 | Frey |
| 2009/0118772 A1 | 5/2009 | Diederich et al. |
| 2009/0216277 A1 | 8/2009 | Tornier et al. |
| 2009/0254125 A1 | 10/2009 | Predick |
| 2009/0264926 A1 | 10/2009 | Taylor et al. |
| 2009/0299411 A1 | 12/2009 | Laskowitz et al. |
| 2010/0030270 A1 | 2/2010 | Winslow et al. |
| 2010/0036417 A1 | 2/2010 | James et al. |
| 2010/0036432 A1 | 2/2010 | Ely |
| 2010/0036436 A1 | 2/2010 | Winslow et al. |
| 2010/0042152 A1 | 2/2010 | Semler et al. |
| 2010/0057131 A1 | 3/2010 | Ely et al. |
| 2010/0057135 A1 | 3/2010 | Helges et al. |
| 2010/0057136 A1 | 3/2010 | Helges et al. |
| 2010/0094345 A1 | 4/2010 | Saidha et al. |
| 2010/0121381 A1 | 5/2010 | Berta |
| 2010/0160981 A1 | 6/2010 | Butler et al. |
| 2010/0222822 A1 | 9/2010 | Farris et al. |
| 2010/0280552 A1 | 11/2010 | Lee |
| 2010/0298884 A1 | 11/2010 | Faizan et al. |
| 2011/0137345 A1 | 6/2011 | Stoll et al. |
| 2011/0178558 A1 | 7/2011 | Barry |
| 2011/0190824 A1 | 8/2011 | Gephart |
| 2011/0213419 A1 | 9/2011 | Richelsoph |
| 2011/0218579 A1 | 9/2011 | Jackson |
| 2012/0095510 A1 | 4/2012 | Nihalani |
| 2012/0095511 A1 | 4/2012 | Nihalani |
| 2012/0123478 A1 | 5/2012 | Winslow et al. |
| 2012/0150230 A1 | 6/2012 | Felix et al. |
| 2012/0226316 A1 | 9/2012 | Dant et al. |
| 2012/0253400 A1 | 10/2012 | Clark et al. |
| 2012/0253401 A1 | 10/2012 | Clark et al. |
| 2012/0253402 A1 | 10/2012 | McLean |
| 2012/0277806 A1 | 11/2012 | Smith et al. |
| 2012/0283778 A1 | 11/2012 | Yeh |
| 2013/0023932 A1 | 1/2013 | Helgerson |
| 2013/0103092 A1 | 4/2013 | Ballard |
| 2013/0165976 A1 | 6/2013 | Gunn |
| 2013/0172934 A1 | 7/2013 | Walker et al. |
| 2013/0184759 A1 | 7/2013 | Rinehart et al. |
| 2013/0325069 A1 | 12/2013 | Pereiro de Lamo et al. |
| 2014/0012333 A1 | 1/2014 | Tornier et al. |
| 2014/0018866 A1 | 1/2014 | Jankovic et al. |
| 2014/0135839 A1 | 5/2014 | Frankel |
| 2014/0180338 A1 | 6/2014 | Triplett |

* cited by examiner

PERCUTANEOUS PEDICLE SCREW REVISION SYSTEM

PRIORITY CLAIM

In accordance with 37 CFR 1.76, a claim of priority is included in an Application Data Sheet filed concurrently herewith. Accordingly, the present invention is a division of U.S. application Ser. No. 15/440,877 filed on Feb. 23, 2017 which is a division of U.S. application Ser. No. 14/341,358 filed on Jul. 25, 2014 and claims priority to U.S. Provisional Patent Application No. 61/858,431, entitled "PERCUTANEOUS PEDICLE SCREW REVISION SYSTEM", filed Jul. 25, 2013. The contents of which the above referenced application is incorporated herein by reference.

FIELD OF THE INVENTION

The instant invention relates to surgical instruments useful in bone fixation procedures and methods of use thereof; and more particularly to a system and devices for percutaneously revising existing pedicle screw assemblies for adding additional levels.

BACKGROUND OF THE INVENTION

The central nervous system is a vital part of the human physiology that coordinates human activity. It is primarily made up of the brain and the spinal chord, with the spinal chord acting as a conduit to communicate neuronal signals from the brain to the rest of the body, including motor control and sensations. Protecting the spinal chord is the spinal, or vertebral, column. While most people have fully functional spinal chords, it is not uncommon for individuals to suffer some type of spinal ailment, including spondylolisthesis, scoliosis, or spinal fractures. In severe cases where non-surgical procedures are not effective, or for cases which have developed into spinal instability or severe disc degeneration, surgical intervention may be required.

There are many different approaches taken to alleviate or minimize severe spinal disorders. One surgical procedure commonly used is a spinal fusion technique. Spinal fusion is a standard back surgical technique and its use continues to rise. In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse.

While spinal fixation procedures can have positive outcomes, adjacent segment degeneration (ASD) often follows fusion surgeries. In addition to requiring the fusion of additional spinal segments, patients suffering from ASD often require posterior pedicle screw rod fixation. Such cases can be difficult for the surgeon as the surgical procedure often requires "opening" of the patient's back to expose the entire system in order for the surgeon to get to the top tulip. Such procedure is not beneficial to the patient as it exposes them to increased pain, higher morbidity, worsening of paraspinal muscle fibrosis/atrophy. Should the surgeon need to completely remove the old system, trying to remove an existing rod in order to provide a new construct can be technically difficult. Moreover, given the number of different spinal fixation systems in the market, knowing what system the patient contains and having the right tools to work on that system is a challenge.

There exists, therefore, a need for an improved devices and systems for extending a patient's existing fixation hardware which does not require open dissection, reduces the disruption of post tension bands, and can be used with any existing pedicle screw system in place.

SUMMARY OF THE INVENTION

The present invention describes a system, devices and methods for percutaneous pedicle screw revision procedures. The present invention utilizes a tulip rod stub/connector adapted to be used to extend pedicle screw/rod constructs with minimal disruption to surrounding soft tissue and without having to remove existing hardware. Connecting to already existing systems minimizes secondary exposure risks and preserves soft tissue and natural elements of the posterior tension bands. While current extension procedures are preformed using an open procedure, the present invention provides for a percutaneous approach.

Accordingly, it is an objective of the present invention to provide a system, devices, and methods for providing percutaneous pedicle screw revision techniques.

It is a further objective of the present invention to provide a system, devices, and methods for extending screw/rod constructs with minimal disruption of surrounding soft tissue.

It is yet another objective of the present invention to provide a system, devices, and methods for extending screw/rod constructs without removing existing hardware.

It is a still further objective of the invention to provide a system, devices, and methods for extending screw/rod constructs without requiring instruments used in constructing the original spinal construct to be used in the extension procedure.

It is a further objective of the present invention to provide a system, devices, and methods for extending screw/rod constructs adapted to connect to any screw/rod based system.

It is yet another objective of the present invention to provide a system, devices, and methods for extending screw/rod constructs which minimize secondary exposure risks and disruption of posterior tension bands.

It is a still further objective of the invention to provide a device capable of connecting an existing spinal rod construct and new spinal rod.

It is a further objective of the present invention to provide a device capable of connecting an existing spinal rod construct and new spinal rod which includes a device using pinchers or jaws to secure the existing spinal rod implant.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
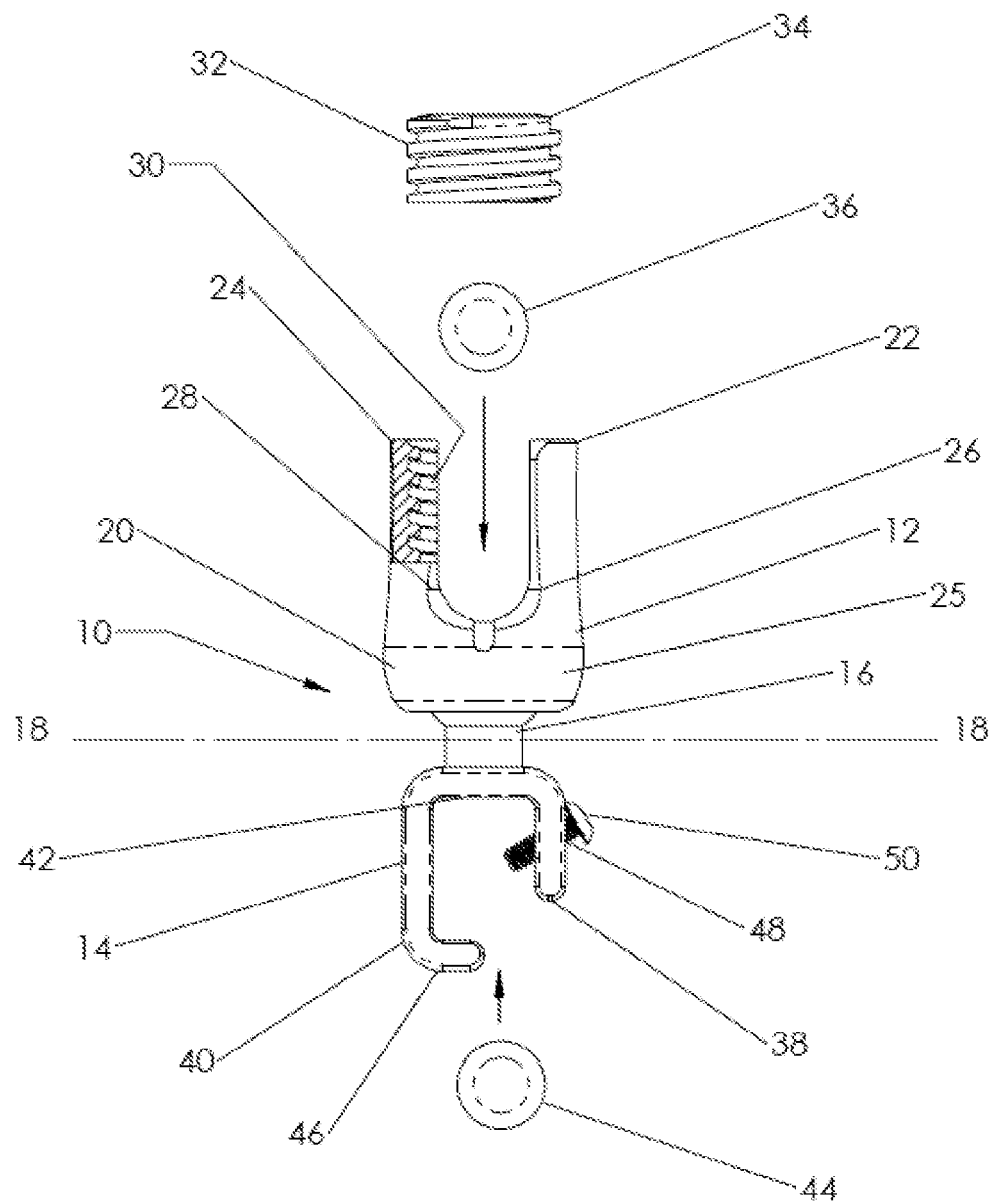
FIG. 1 illustrates an embodiment of the tulip rod stub/connector in accordance with the present invention.

While the present invention is susceptible of embodiment in various forms, there is shown in the drawings and will hereinafter be described a presently preferred, albeit not limiting, embodiment with the understanding that the present disclosure is to be considered as exemplification of the present invention and is not intended to limit the invention to the specific embodiments illustrated.

The present invention provides a system, devices, and methods for extending an existing spinal construct using a percutaneous approach. The present invention, therefore, is designed to provide methods for extending post pedicle screw rod fusion constructs which can be placed in any patient regardless of the type of pedicle screws/rods used.

Referring to FIG. 1, an illustrative example of a device for extending an existing spinal construct, referred to generally as a tulip rod stub/connector 10 is shown. The tulip rod stub/connector 10 contains a first member 12, sometimes referred to as rod engagement member, and a second member 14, sometimes referred to as existing spinal construct engagement member, and an intermediate member 16 connecting the first member 12 and the second member 14. The first member is constructed and arranged to engage "newly added spinal hardware"; the second member is constructed and arranged to engage "existing spinal hardware." The tulip rod stub/connector 10 is used to provide extension of spinal hardware from spinal hardware already existing, i.e. "existing spinal hardware" defined as spinal implants previously inserted into a patient to hardware to be inserted into the patient, i.e. "newly added spinal hardware" defined as hardware to be inserted to address new ailments or to correct a new problem. In the embodiment illustrated in FIG. 1, the first member 12 and the second member 14 are arranged in a centered orientation where the first member is positioned above a center horizontal longitudinal line axis 18 and the second member 14 is positioned below the horizontal longitudinal line axis 18.

The first member 12 contains a saddle or tulip 20 having two generally parallel arms 22 and 24 extending in an upward direction from a base 25. The inner surfaces 26 and 28 of the arms 22 and 24 contain threading 30 adapted to receive corresponding threading 32 of a set screw 34. The tulip 20 is generally sized and shaped to receive a new spinal rod 36 which, when inserted therein is secured and fastened to the base 25 via the set screw. The second member 14 contains two generally parallel arms 38 and 40 separated by the base 42. The second member 14 is designed to receive a surgical rod 44 existing from a previous construct within a patient. To aid in securing the rod 44 to the second member 14, the arm 40 contains a hooked portion 46. In addition, inserted into opening 48 positioned within arm 38 is a screw 50. Once the rod 44 is inserted into the second ember 14, it is fastened in place by rotation of the screw 50.

The tulip rod stub/connector 10 is shown so that the first member and the second member are to be fixed in place. However, an alternative embodiment of the tulip rod stub/connector 10 includes a first member constructed and arranged to rotate or spin 360 degrees about the intermediate portion 16. The tulip rod stub/connector 10 may also contain an intermediate member 16 which has a concave female socket 52 for engaging a bulbous (spherical) male end 54 located on the tulip 20, see FIG. 2. The female socket and the male end 54 secure together or couple to provide a poly-axial tulip, allowing the tulip to rotate and be orientated in multiple directions.

Figure 3:
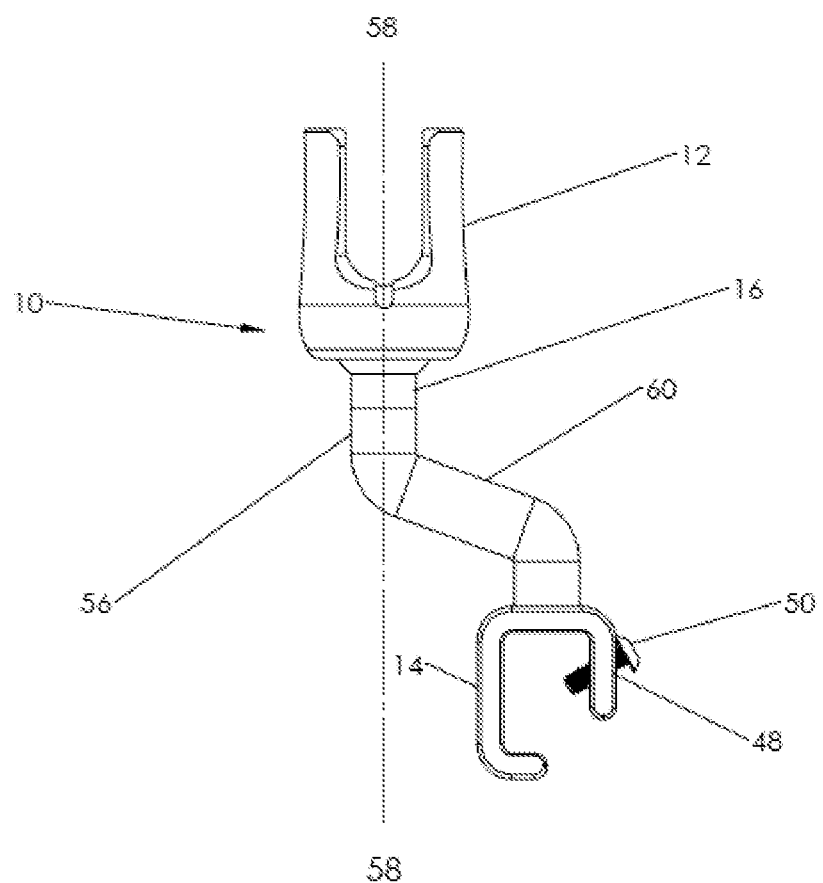
FIG. 3 is an alternative embodiment of the tulip rod stub/connector in accordance with the present invention having an offset orientation.

Referring to FIG. 3, an alternative embodiment of the tulip rod stub/connector 10 is illustrated. The tulip rod stub/connector 10 has all the same features as described for the tulip rod stub/connector 10 illustrated in FIG. 1, however, the tulip rod stub/connector 10 includes the second member 14 being positioned in an offset relationship to the first member 12. In this embodiment, the intermediate portion 16 comprises a first intermediate portion 56 aligned with the vertical longitudinal axis 58 and a second intermediate portion 60 angled from the first member 56. The second intermediate portion 60 is coupled to the second member 14 whereby the second member 14 is positioned in an offset orientation, or off-center from the vertical longitudinal axis 58, and in effect from the first member 12. This orientation allows a new spinal rod to be attached to previous constructs when such relationship is not linear.

The tulip rod stub/connector 10 may be constructed to have both the first member 12 and the second member 14 fixed in position. Alternatively, the first member 12 may be constructed to rotate or spin 360 degrees about the first intermediate portion 56. Alternatively, tulip rod stub/connector 10 may be constructed to include a poly-axial tulip, allowing the tulip to rotate and be orientated in multiple directions.

Figure 4:
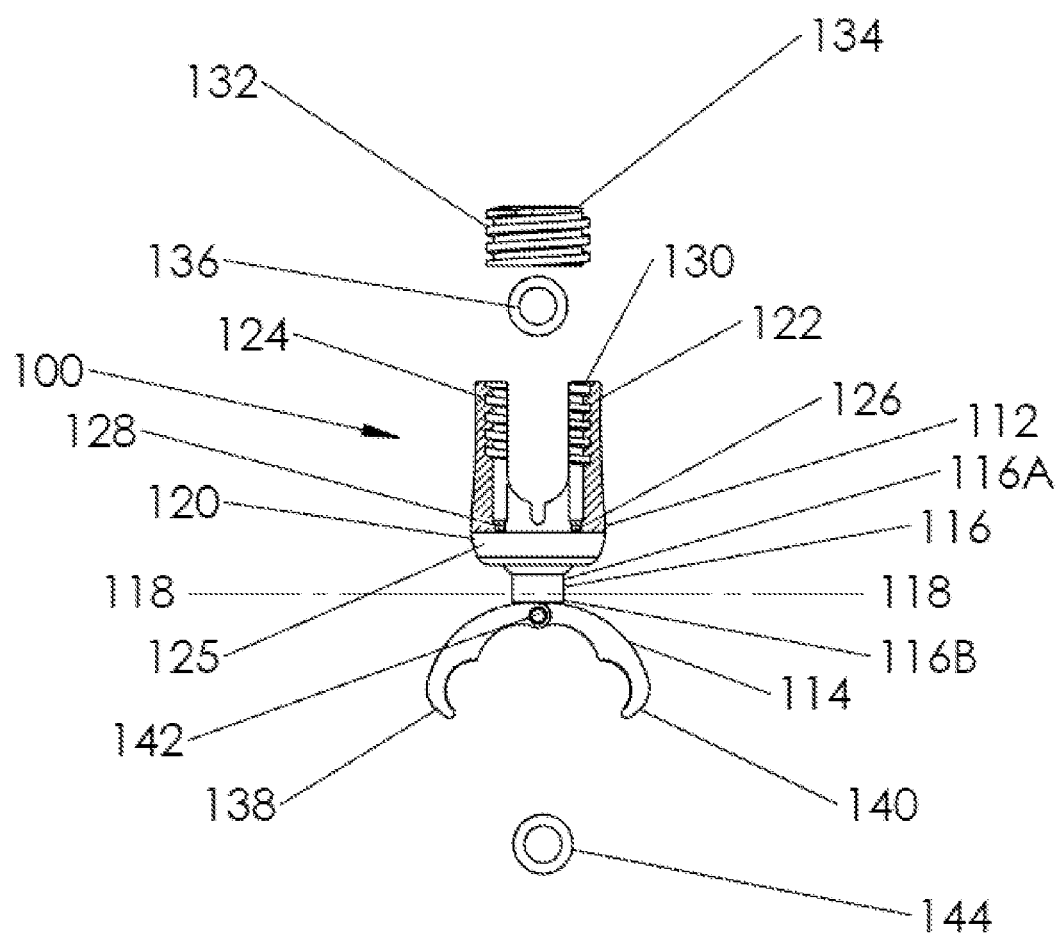
FIG. 4 is an alternative embodiment of the tulip rod stub/connector, illustrating the use of pinchers or jaws.

Referring to FIG. 4, an alternative embodiment of the tulip rod stub/connector 10, referred to generally as 100, is illustrated. The tulip rod stub/connector 100 contains a first member 112, sometimes referred to as rod engagement member, and a second member 114, sometimes referred to as existing spinal construct engagement member, and an intermediate member 116 connecting the first member 112 and the second member 114. The first member is constructed and arranged to engage "newly added spinal hardware"; the second member is constructed and arranged to engage "existing spinal hardware." In the embodiment illustrated in FIG. 4, the first member 112 and the second member 114 are arranged in a centered orientation where the first member 112 is at one end (116A) of the intermediate portion 116, above a center horizontal longitudinal line axis 118, and the second member 114 is positioned at an opposing end (116B) of the intermediate portion 116, below the horizontal longitudinal line axis 118.

The first member 112 contains a saddle or tulip 120 having two generally parallel arms 122 and 124 extending in an upward direction from a base 125. The inner surfaces 126 and 128 of the arms 122 and 124 contain threading 130 adapted to receive corresponding threading 132 of a set screw 134. The tulip 120 is generally sized and shaped to receive a new spinal rod 136 which, when inserted therein, is secured to and fastened to the base 125 via the set screw 134. The second member 114 contains two pinchers or jaws 138 and 140. The movable pinchers or jaws 138 and 140 are secured together by a pin 142 and are designed to move inwardly towards each other in a uniform or non-uniform manner to form a closed position, and outwardly, or away from each other, to form an open position using an actuation mechanism.

Figure 2:
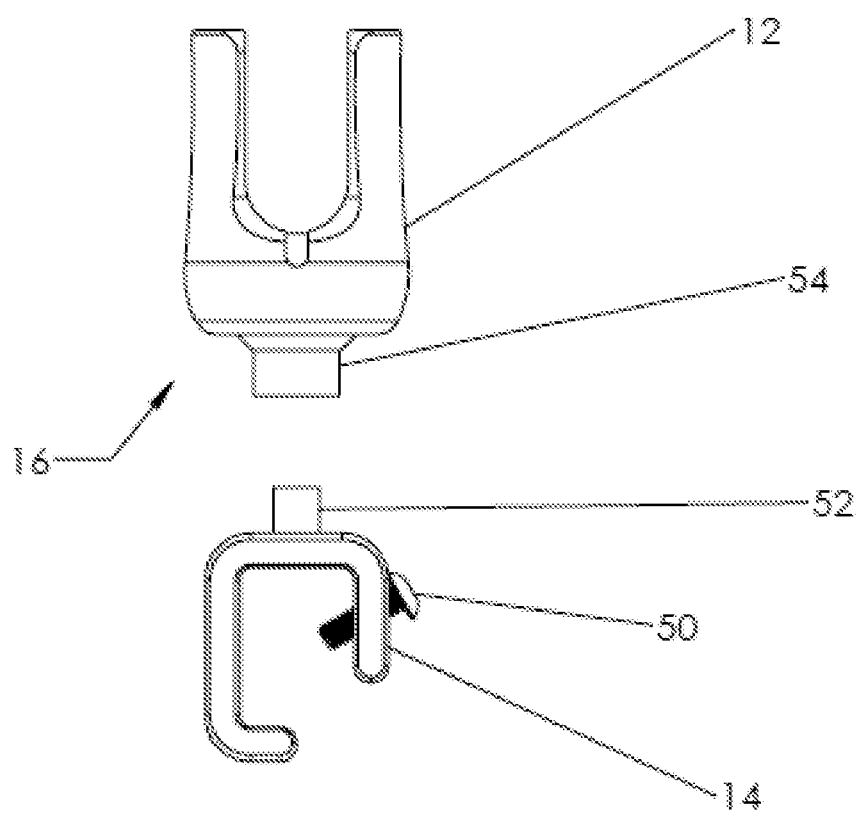
FIG. 2 is an alternative embodiment of the tulip rod stub/connector shown in FIG. 1, having a poly-axial tulip.

The second member 114 is designed to receive a surgical rod 144 existing from a previous construct within a patient. To aid in securing the rod 144 to the second member 114, the jaw 140 contains a hooked end 146. The tulip rod stub/connector 100 is shown so that the first member 112 and the second member 114 are to be fixed in place. However, an alternative embodiment of the tulip rod stub/connector 100 includes a first member 114 constructed and arranged to rotate or spin 360 degrees about the intermediate portion 116. The tulip rod stub/connector 100 may also contain an intermediate member 116 which has a concave female socket (not shown) for engaging a bulbous (spherical) male end (not shown) but located on the tulip 120, similar to the tulip rod stub/connector 10 as illustrated in FIG. 2 and previously described. The female socket and the male end secure together to provide a poly-axial tulip, allowing the tulip to rotate and be orientated in multiple directions.

Figure 5:
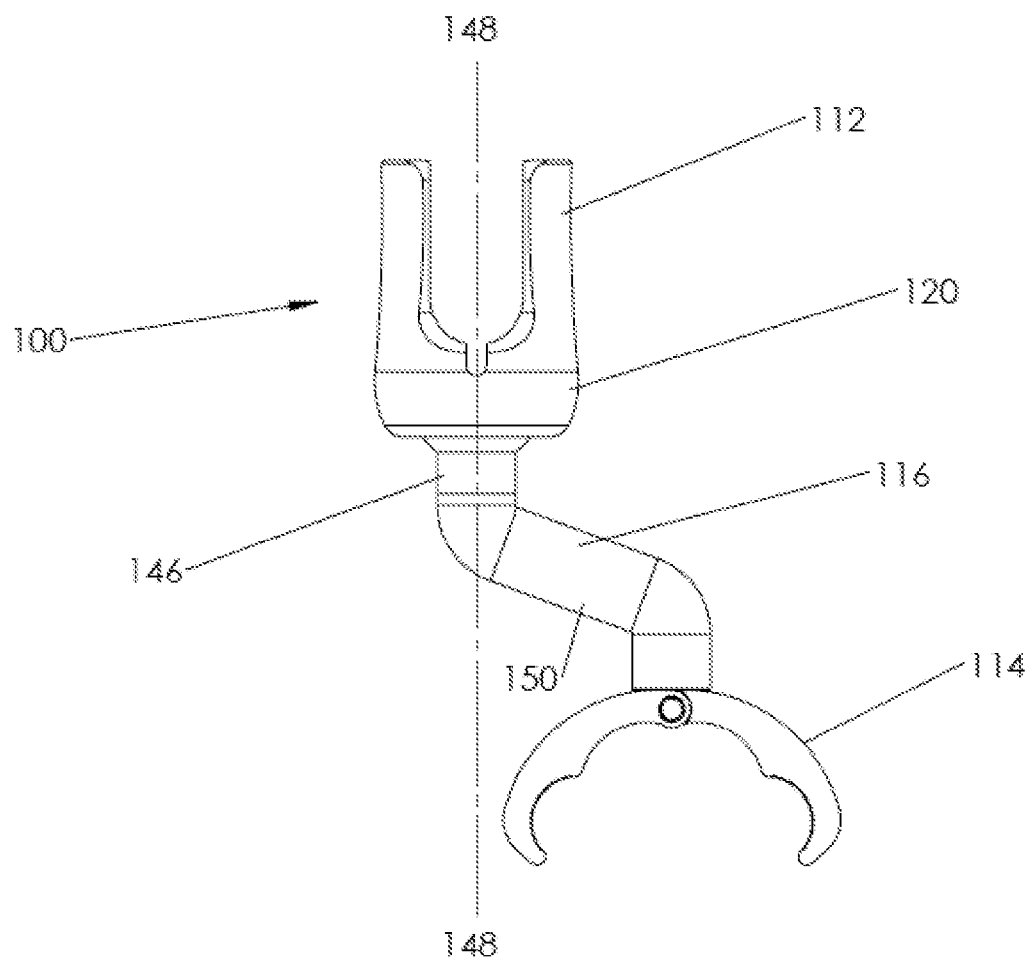
FIG. 5 is an alternative embodiment of the tulip rod stub/connector illustrated in FIG. 4 having an offset orientation.

Referring to FIG. 5, an alternative embodiment of the tulip rod stub/connector 100 is shown. The tulip rod stub/connector 100 has all the same features as described for the tulip rod stub/connector 100 illustrated in FIG. 4, however, the tulip rod stub/connector 100 includes the second member 114 being positioned in an offset relationship to the first member 112. In this embodiment, the intermediate portion 116 comprises a first intermediate portion 146 aligned with a vertical longitudinal axis 148, and a second intermediate portion 150 angled from the first intermediate portion 146. The second intermediate portion 150 is coupled to the second member 114, whereby the second member 114 is positioned in an offset orientation, or off-center from the vertical longitudinal axis 148, and in effect from the first member 112.

This orientation allows a new spinal rod to be attached to previous constructs where such relationship or alignment is not linear. The tulip rod stub/connector 100 may be constructed to have both the first member 112 and the second member 114 fixed in position. Alternatively, the first member 112 may be constructed to rotate or spin 360 degrees about the first intermediate portion 146. Alternatively, the tulip rod stub/connector 100 may be constructed to include a poly-axial tulip, allowing the tulip 120 to rotate and be orientated in multiple directions.

Figure 6:
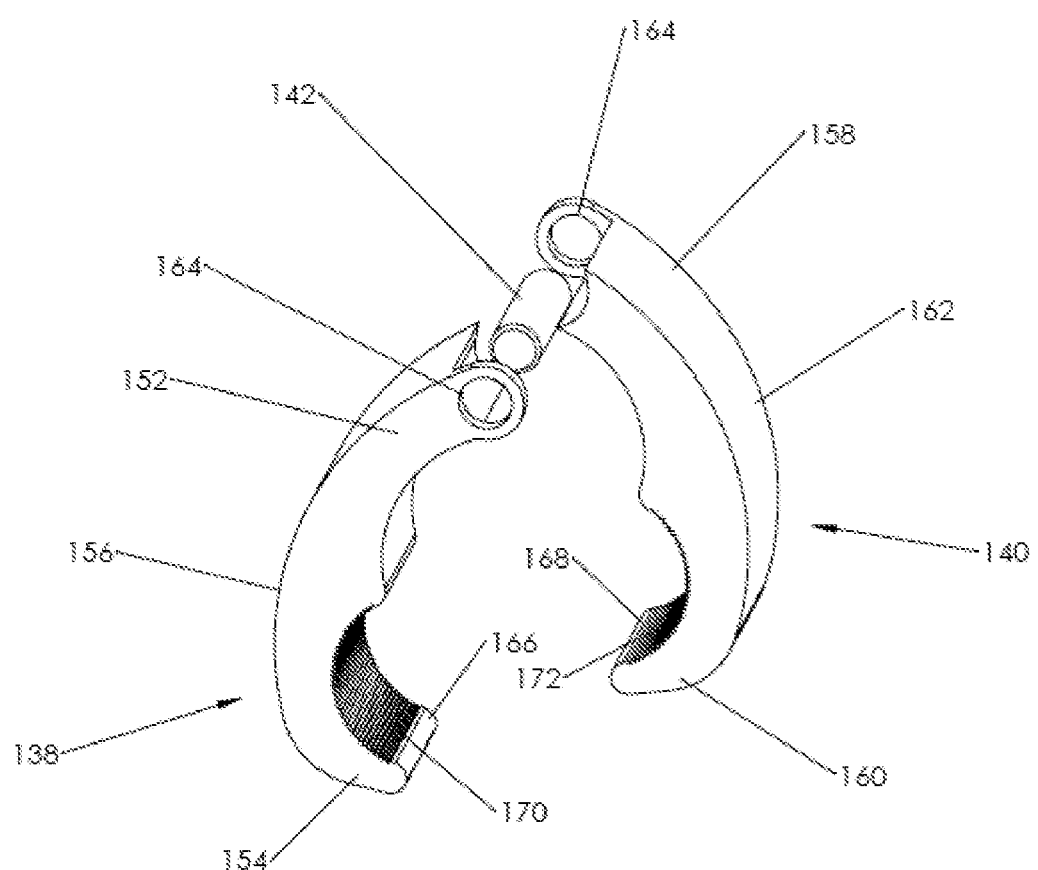
FIG. 6 is an exploded view of the pinchers or jaws in accordance with the present invention.

Referring to FIG. 6, an illustrative example of pinchers or jaws 138 and 140 are shown. Pincher or jaw 138 contains a first end 152, a second end 154, and a main body 156. Pincher or jaw 140 contains a first end 158, a second end 160, and a main body 162. The first ends 152 and 158 contain an opening 164 sized and shaped to receive a pin 142 which, when placed side by side, allow for the pin to secure jaws 138 and 140 in a hinged and movable orientation. At or near the second ends 154 and 160 are opposing concave surfaces 166 and 168 sized and shaped to the contour of a cylindrical rod, and are used to secure spinal rods within. Each of the concave surfaces 166 and 168 may but need not contain a plurality of teeth 170, 172 for providing better gripping of an inserted rod.

Figure 7:
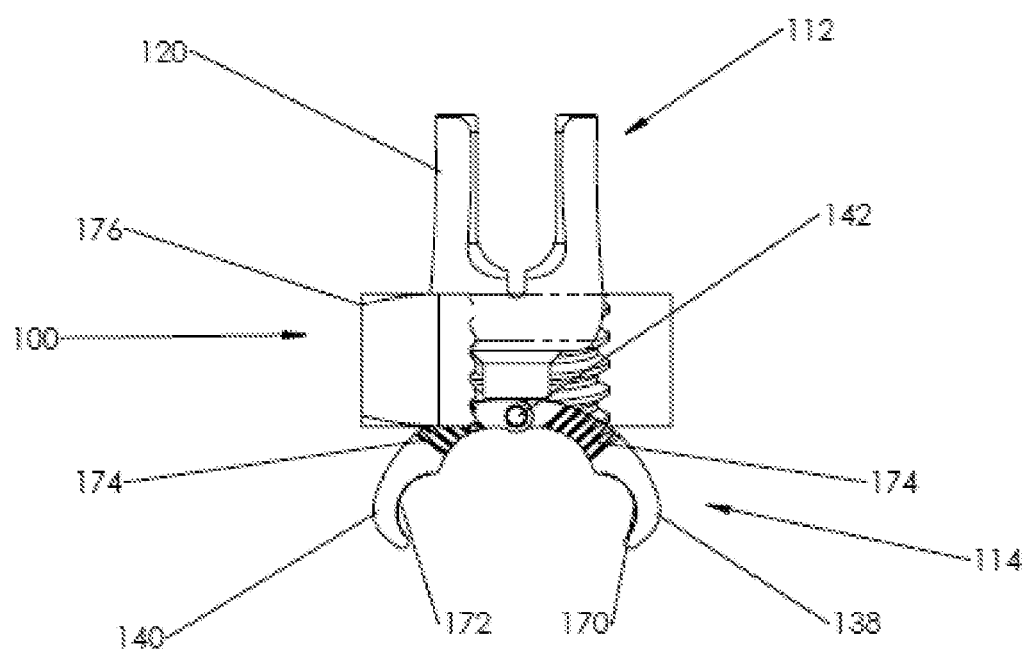
FIG. 7 is an example of the tulip rod stub/connector having an illustrative mechanism to actuate the jaws between the closed and open position.

Referring to FIG. 7, an illustrated example of a mechanism to actuate the jaws 138 and 140 between the closed and open position is shown. While the example shows a tulip rod stub/connector 100 similar to that described in FIG. 4, such mechanism may be applicable to other embodiments. As illustrated, the outer surfaces 170 and 172 of jaws 138 and 140 contain threading 174. To actuate the jaws 138 and 140 to a closed position, the tulip rod stub/connector 100 further includes a nut 176 placed on the outside of the first member 112. As the nut 176 is directionally moved, squeezing against each jaw 138 and 140, they move inwardly toward each other. Should a rod be positioned between the jaws 138 and 140, movement inward secures and locks the jaws 138 and 140 against it. Moving the nut 176 in the opposite direction results in the jaws 138 and 140 moving in an opposite direction, away from each other.

Figure 8:
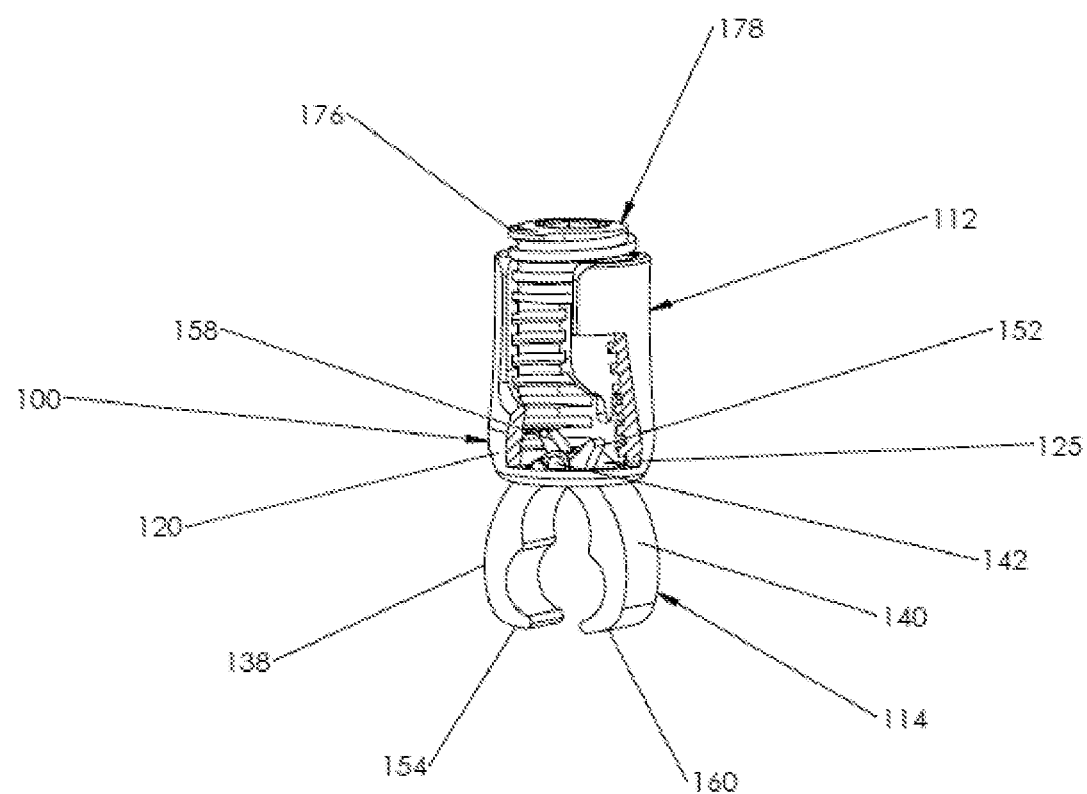
FIG. 8 is an example of the tulip rod stub/connector having an alternative mechanism to actuate the jaws between the closed and open position.

Referring to FIG. 8, an alternative example of a mechanism to actuate the jaws 138 and 140 between the closed and open position is illustrated. While the example shows a tulip rod stub/connector 100 similar that described in FIG. 4, such mechanism may be applicable to other embodiments. In this mechanism, the nut 176 is inserted into the interior 178 of the tulip 120. As the nut is rotated and moves down toward the base 125, portions of the jaws first ends 152, 158 of jaws 138, 140 are contacted by the nut 176. Once in contact, as the nut 176 is further rotated, the first ends 152, 158 are drawn closer to each other, causing the second ends 154 and 160 to move toward each other and eventually clamp down on an inserted rod. Moving the nut 176 in the opposite direction results in the first ends 152, 158 to move away from each other, resulting in the second ends 154 and 160 to move away as well.

Figure 9:
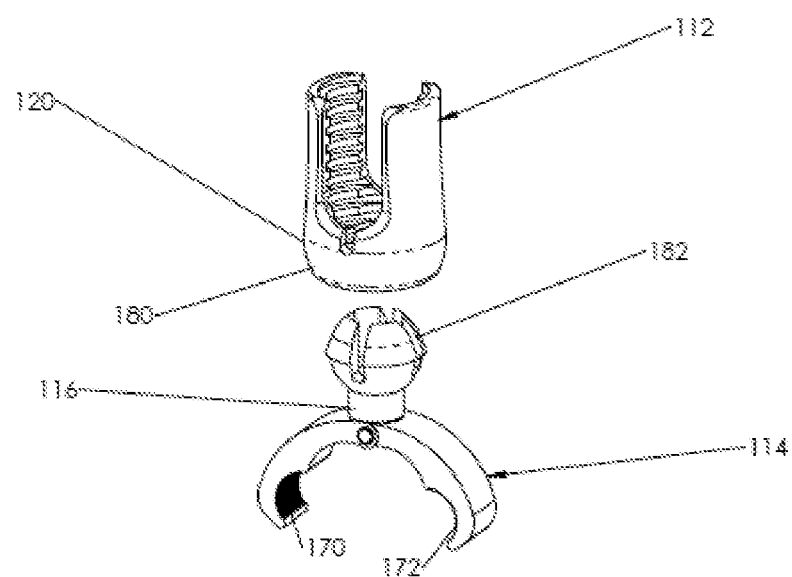
FIG. 9 is an illustrative example of a modular tulip rod stub/connector in accordance with the present invention.

Referring to FIG. 9, an alternative embodiment of the tulip rod stub/connector 100 is shown. The tulip rod stub/connector 100 illustrates a modular feature so that the first portion 112 and the second portion 114 can fit together to form a unitary unit at the site of surgery. As illustrated in FIG. 9, the tulip 120 contains a molded undercut 180 which engages a mated lip 182 within the intermediate portion 116. The mated lip 182 is sized and shaped to snap fit or frictionally fit within the molded undercut 180.

Figure 10A:
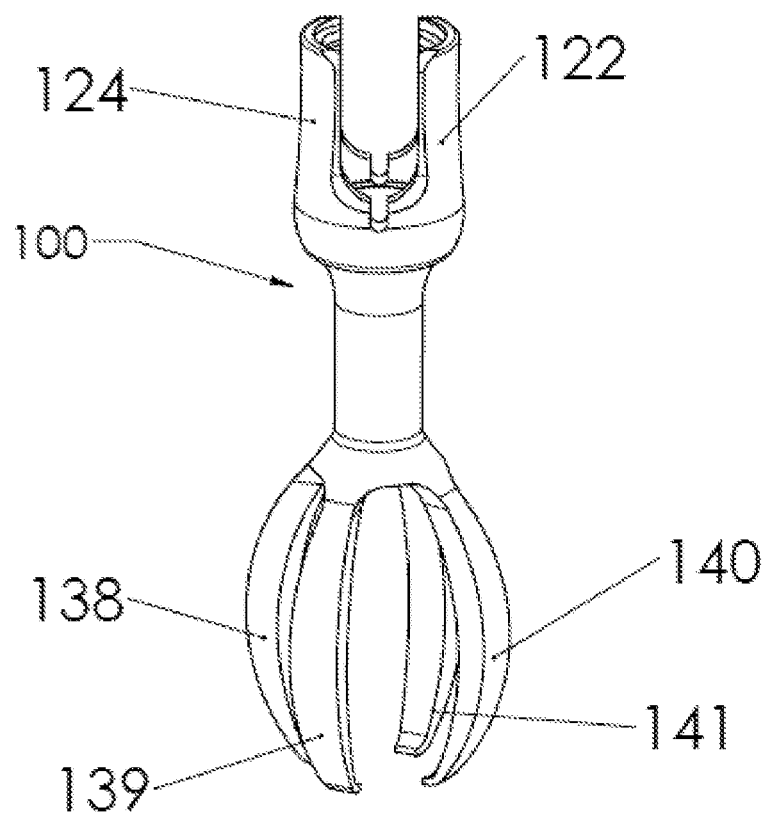
FIG. 10A is an illustrative example of the tulip rod stub/connector having 4 pinchers or jaws.
Figure 10B:
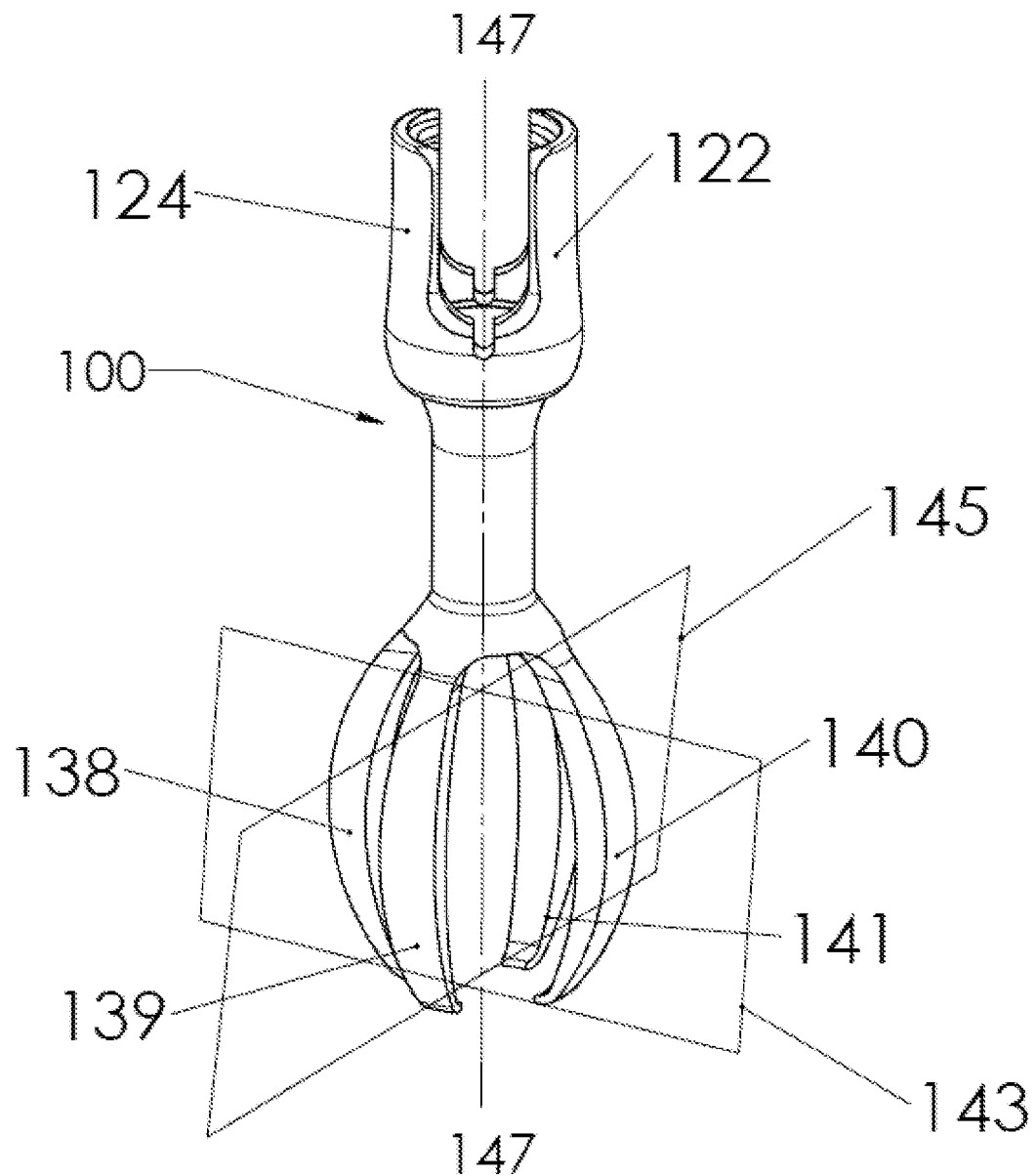
FIG. 10B illustrates the orientation of the pinchers or jaws about a longitudinal axis.
Figure 11:
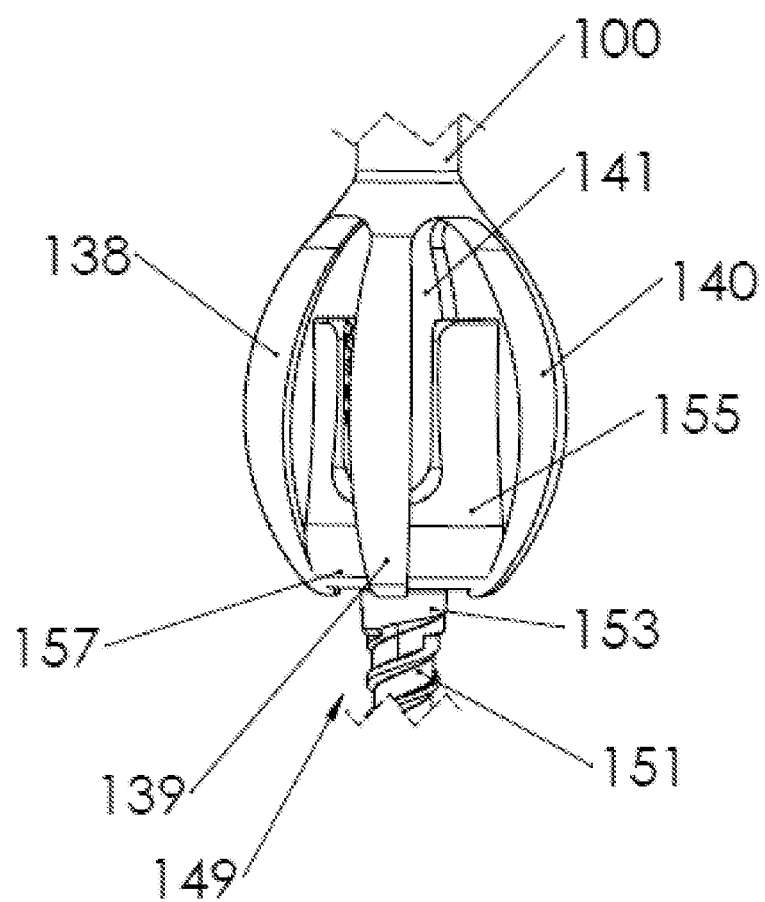
FIG. 11 shows an illustrative the interaction between an existing pedicle screw and tulip rod stub/connector having 4 pinchers or jaws, as shown, the pinchers or jaws engage with and lock underneath a tulip.
Figure 12:
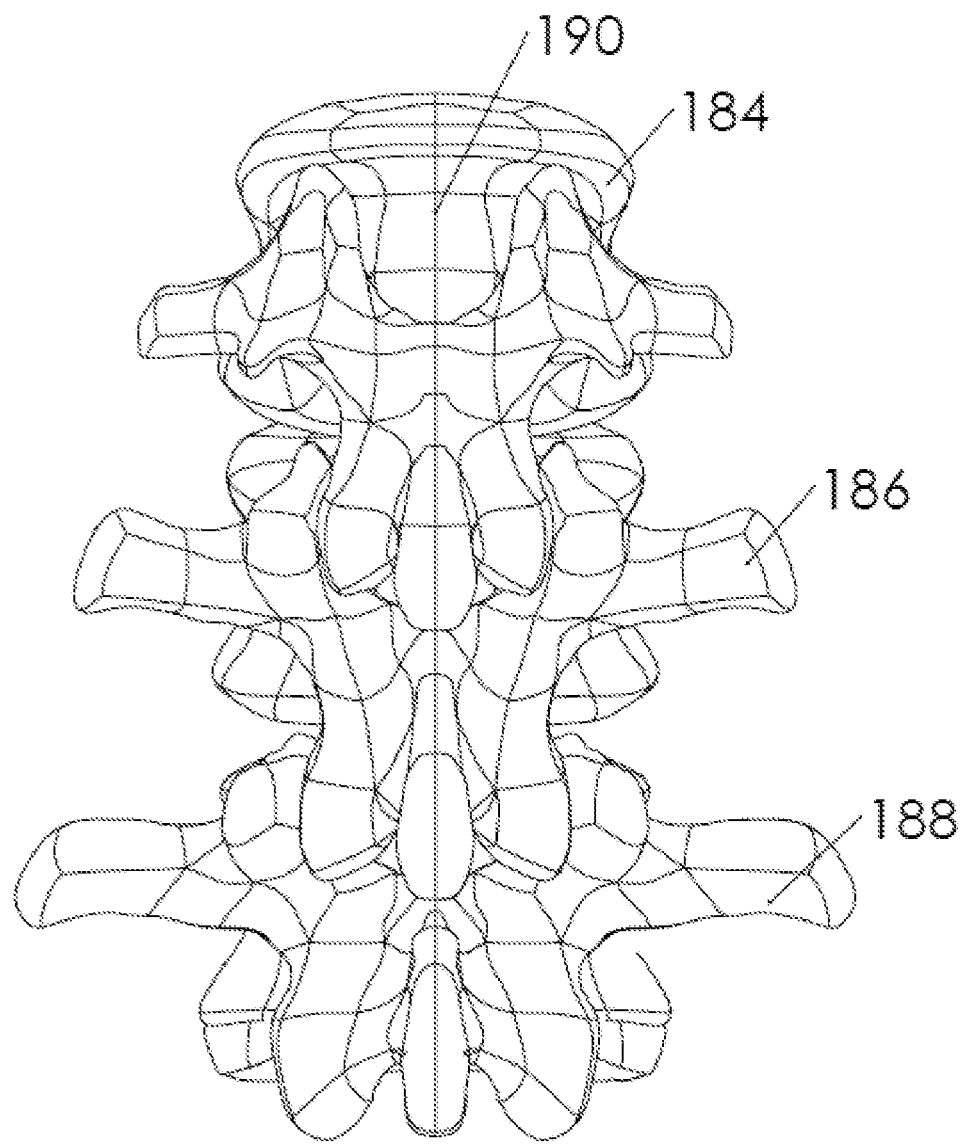
FIG. 12 illustrates several vertebral bodies without spinal fusion devices.
Figure 13:
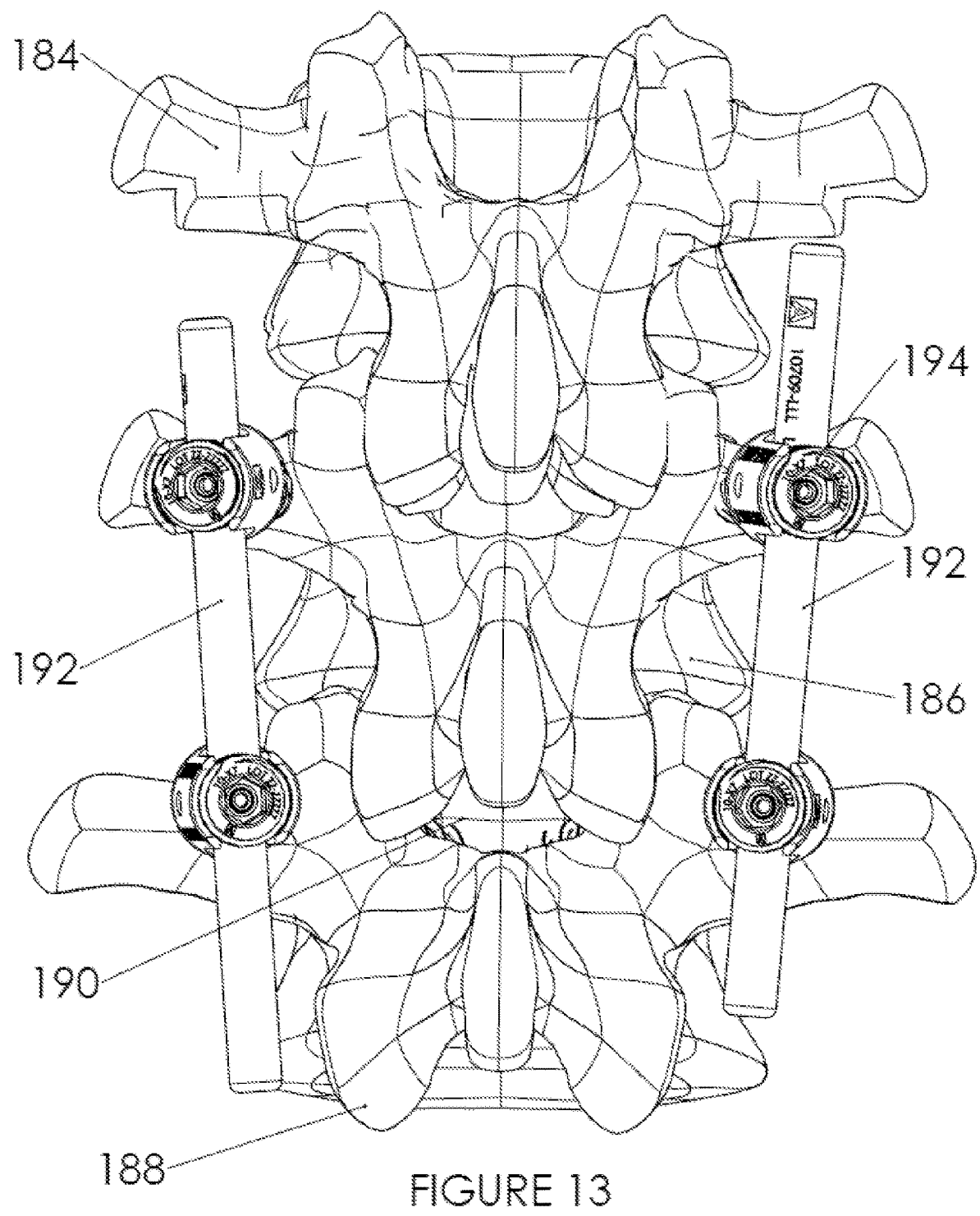
FIG. 13 illustrates several vertebral bodies having previous spinal fusion constructs.

FIGS. 10A and 10B illustrate the tulip rod stub/connector 100 having multiple movable pinchers or jaws. The tulip rod stub/connector 100 having multiple movable pinchers or jaws may take on any configuration as previously described, such as the configurations described and shown in FIG. 4-9. In addition to the movable pinchers or jaws 138 and 140, the tulip rod stub/connector 100 having multiple movable pinchers or jaws is configured to contain two additional movable pinchers or jaws 139 and 141. The pinchers or jaws 138 and 140 may be positioned oppositely about a plane 143 and aligned in a parallel manner, see FIG. 10B. The pinchers or jaws 139 and 141 may be positioned oppositely about a second plane 145 and in a parallel manner. The second plane 145 preferably has a different orientation about a longitudinal axis 147 than the first plane 141. The pinchers or jaws 139 and 141 may be sized and shapes as that of the pinchers 138 or 140 or may be of a different size or shape, i.e. larger or smaller. The tulip rod stub/connector 100 having 4 pinchers or jaws may be secured to a rod. Alternatively, or in addition thereto, the tulip rod stub/connector 100 having 4 pinchers or jaws may be used to connect to a pre-existing, implanted pedicle screw. In this manner, the tulip rod stub/connector 100 having 4 pinchers or jaws can be secured to a implanted tulip. Referring to FIG. 11, the tulip connector 100 having 4 pinchers or jaws is shown engaged with or coupled to an pedicle screw 149 with screw body 151 having threading 153. As shown, each of the pinchers or jaws 138, 140 and 139, 141 engage with the tulip 155 and lock on the bottom or underneath surface 157 of the tulip 155. The pinchers or jaws 138, 140 and 139, 141 may contain serrated surfaces to aid in securing to the bottom surface 157.

Alternative mechanisms for connecting the first portion 112 and the second portion 114 known to one of skill in the art may be used, including but not limited to use of a tab sized and shaped to fit within a slotted region, other snap joints which utilize a protruding part in one of the first portion 112, second portion 114, or intermediate portion 116 designed to deflect as it catches a depression or undercut constructed in the first portion 112, second portion 114, or intermediate portion 116. Once the components are joined together, the snap fit feature is preferably designed to return to a stress-free condition. Alternatively, the individual components, i.e. the first portion 112, the second portion 114, or the intermediate portion 116, may contain threading as a mechanism to secure to each other.

Figure 14:
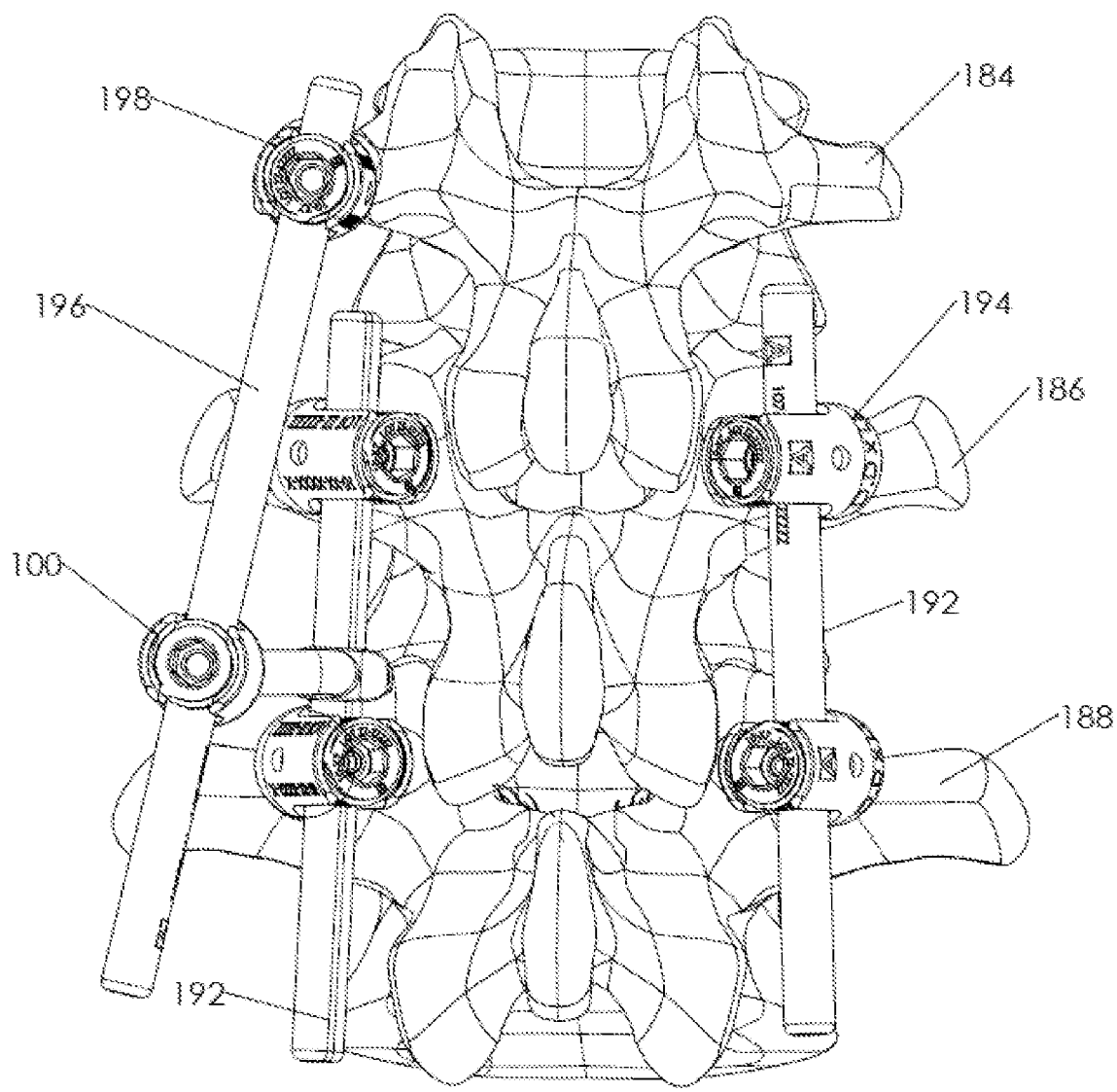
FIG. 14 illustrates the vertebral bodies having previous spinal fusion constructs illustrated in FIG. 4 with new, additional spinal fusion devices.
Figure 16:
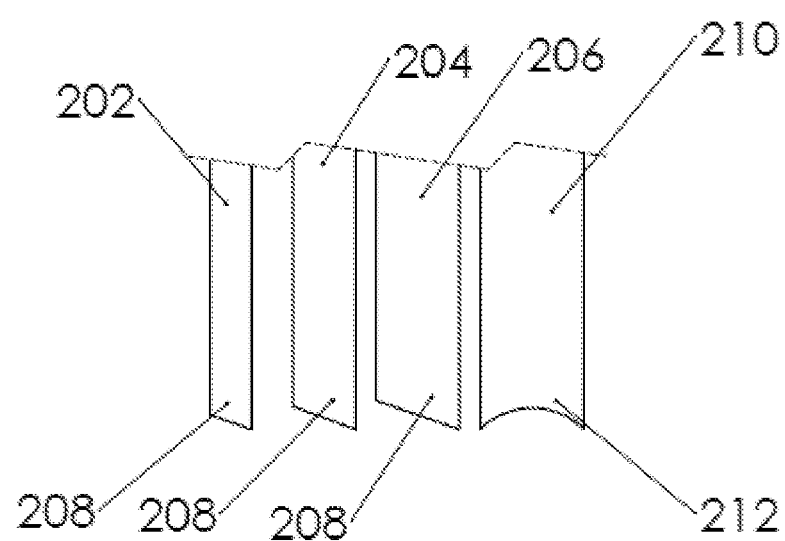
FIG. 16 illustrates a plurality of dilators.

Referring to FIG. 14, a top view of a plurality of vertebral bodies 184, 186, and 188 with spinal canal 190 is shown. FIG. 16 illustrates the vertebral bodies 186 and 188 having spinal fusion devices, such as spinal rods 192 secured by pedicle screws 194, attached thereto and referred to generally as previous constructs 192-194. Referring to FIG. 14, additional, new spinal fusion devices, rod 196, tulip rod stub/connector 100 (or tulip rod stub/connector 10) and new pedicle screw 198 is shown added to the previous constructs 192-194, thereby connecting vertebral body 184 to vertebral bodies 186 and 188.

The present invention is used to extend pedicle screw/rod constructs with minimal disruption to surrounding soft tissue, without having to remove existing hardware. Since the existing hardware remains, the surgeon is not required to use any components of the older system as part of the new surgical procedure. By being able to connect to any already existing system, extension of existing constructs using the present invention minimizes secondary exposure risks and preserves soft tissue and natural elements of the posterior tension bands. While current extension procedures are preformed using an open procedure, the present invention provides for a percutaneous approach.

Figure 15:
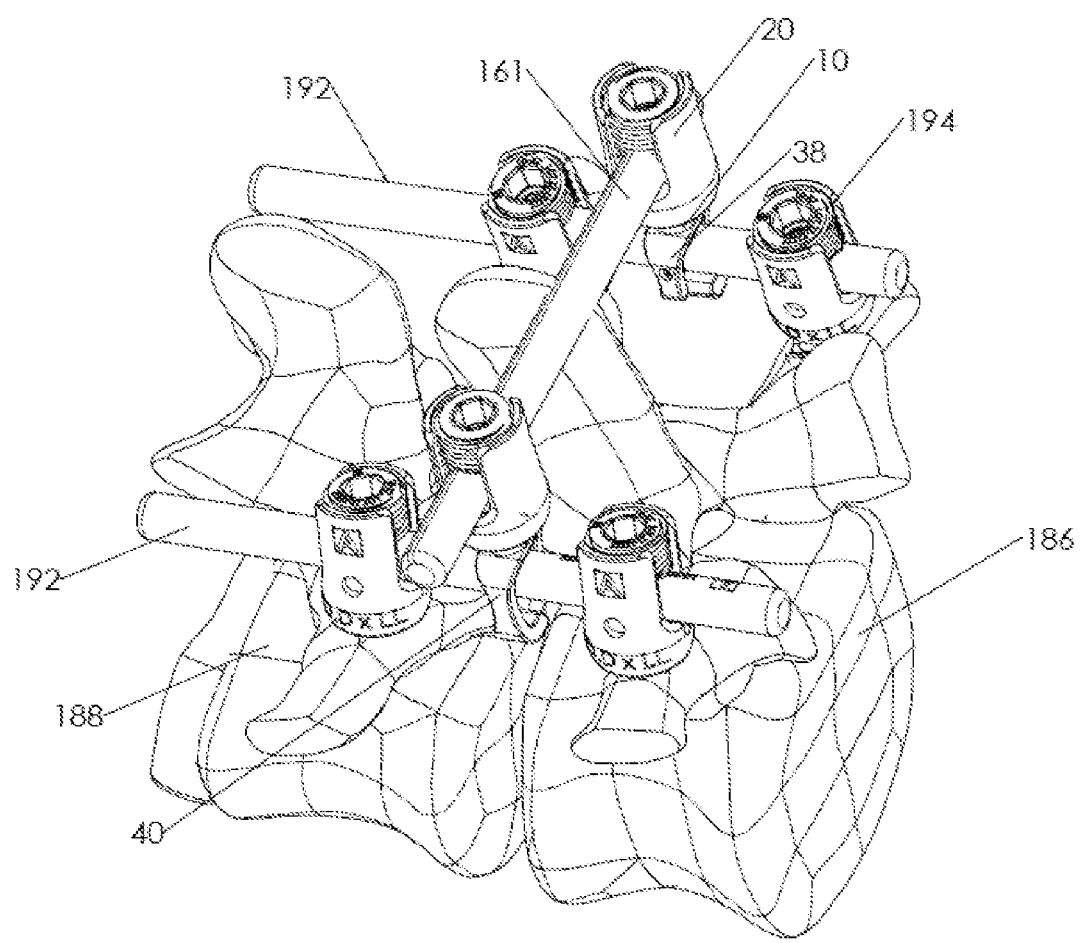
FIG. 15 illustrates the use of the modular tulip rod stub/connector used to connect opposing rods as part of percutaneous cross link system.

Alternatively, or in addition thereto, using the tulip rod stub/connector 10 (or tulip rod stub/connector 100) to extend pedicle screw/rod constructs with minimal disruption to surrounding soft tissue, without having to remove existing hardware, the tulip rod stub/connector 10/100 may be used as a cross-connector to cross-link existing rods. Such cross linking provides torsional stability. Referring to FIG. 15, tulip rod stub/connector 10 is shown with arms 38 and 40 (or pinchers or jaws 138 and 140) secured to rods 192. The rods 192 are secured to vertebral bodies 186 and 188. The saddle or tulip 20, which is positioned above the rod 192, receives and secures spinal rod 161. While only one cross-connector is illustrated, it is understood that multiple cross connections may be used.

In use, the method of extending an existing construct is done percutaneously by passing a blunt dilator to an existing rod of an existing spinal construct. A series of dilators, 202, 204, and 206 (see FIG. 16) each having different diameters can be used. The dilators, 202, 204, and 206, may have a beveled edge 208 at the distal end to be held in place on the rod. Passing a series of the dilators to the site provides the surgeon with a working space. Dilator 210, having a curved surface 212 at the distal end may be used as a tissue distractor, removing any soft tissue at the attachment point of the existing rod. Once the last dilator is in place, the tulip rod stub/connector 10/100 is passed through so that the second member 14/114 is delivered to the existing rod. Depending on the embodiment and the mechanism needed, the tulip rod stub/connector 10/100 is secured tight to the rod. For example, if a nut is used (either externally to the tulip or internally) to actuate the jaws 138 and 140 of the tulip rod stub/connector 100, the nut is passed through the dilator or a separate extension or tower to provisionally tighten against the rod. A new pedicle screw is then placed at the new/adjacent level via known techniques, including for example, using K-wire precutaneous screw delivery systems. The tulip 20/120 and the new pedicle screw tulip are aligned so that the surgeon can pass the new rod from one tulip to another. Lock screws are inserted into each of the tulips and a final tightening is performed.

Figure 17:
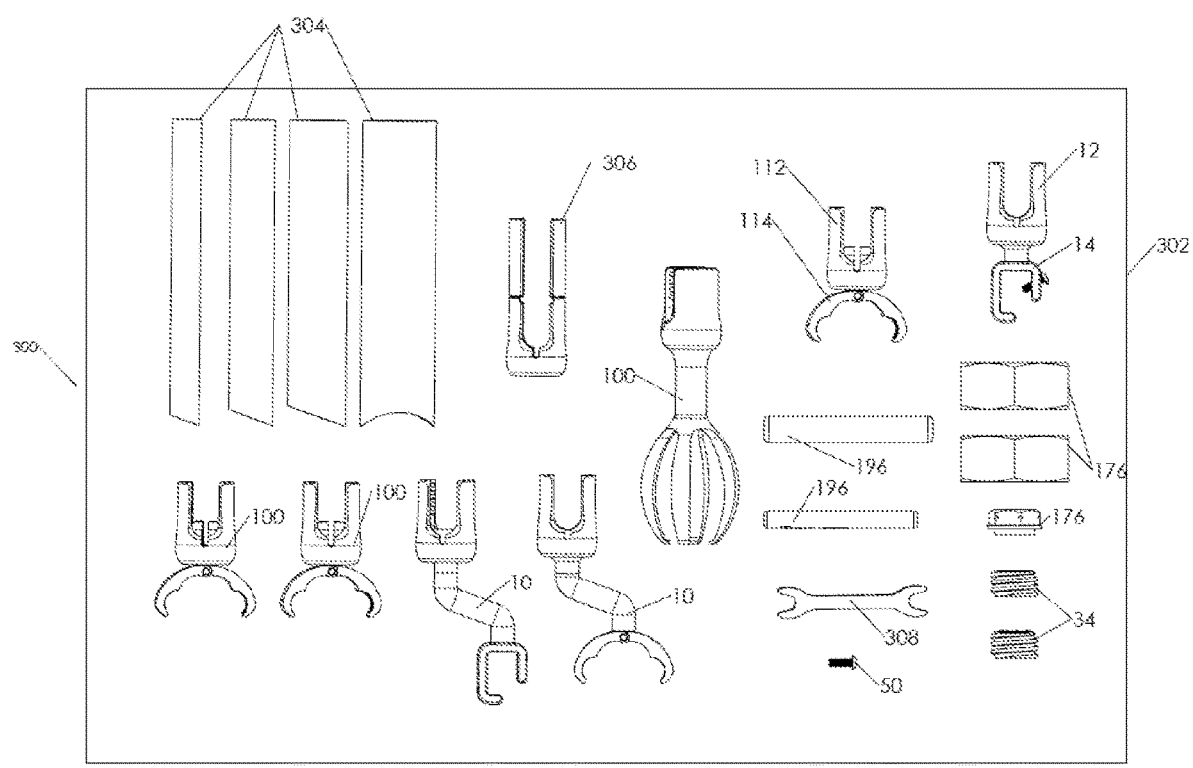
FIG. 17 illustrates a kit including one or more components for use in a spinal revision procedure.

The present invention further contemplates a kit having the necessary components to provide for the percutaneous pedicel screw revision system in accordance with the invention as described herein. FIG. 17 illustrates a kit 300 having a container 302. the container 302 stores a plurality of existing spinal construct extenders 10/100 with different sizes, such as universal clamp, 5/5 clamp, 4/5 clamp, 6/5 clamping, or ¼ inch clamp, having a center orientation, an off-centered orientation, as well as individual first members 12/112 and second members 14/114 for providing for modular devices, or combinations thereof. The kit may also include a plurality of differently sized actuating nuts 176, a plurality of set screws 32 and 50, and a plurality of rods 196. Other hardware may include a set of dilators 304 or extensions/towers 306 and a wrench for engagement with the actuating nuts 176.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for percutaneous pedicle screw revision procedures comprises:
   a first or new spinal rod;
   a tulip rod stub-connector having a first member to engage and connect to the first or new spinal rod and a second member to engage and connect to an existing spinal rod, the first member having a tulip having two generally parallel arms extending from a base and sized to receive the first or new spinal rod and the second member having two arms spaced from the base of the first member and separated by a base of the second member, one of said arms of the second member having a hooked end portion spaced from the opposite arm to form an opening to pass onto an existing spinal rod;
   a screw inclined in a threaded opening of the opposite arm of the second member to fasten the tulip rod stub-connector to the existing spinal rod by pressing the existing spinal rod into and against the one of said arms of the second member having a hooked end portion; and
   wherein the first member and the second member of the tulip rod stub-connector are connected to an intermediate member and the second member is positioned offset relative to the first member.

2. The system for percutaneous pedicle screw revision procedures of claim 1 wherein the intermediate portion has a first intermediate portion aligned with a vertical longitudinal axis of the first member and a second intermediate portion angled from the vertical longitudinal axis of the first member.

3. The system for percutaneous pedicle screw revision procedures of claim 2 wherein the second intermediate portion is coupled to the second member whereby the second member is positioned in an offset orientation from the vertical longitudinal axis of the first member.

4. The system for percutaneous pedicle screw revision procedures of claim 3 wherein an orientation of the first member and the second member allows the first or new spinal rod to be attached to the existing spinal rod where the relationship between the first or new spinal rod and the existing spinal rod are not linear relative to each other.

5. The system for percutaneous pedicle screw revision procedures of claim 1 wherein the first member is constructed and arranged to rotate or spin about the intermediate portion.

6. The system for percutaneous pedicle screw revision procedures of claim 1 wherein the first member is constructed and arranged to rotate or spin 360 degrees about the intermediate portion.

7. The system for percutaneous pedicle screw revision procedures of claim 1 wherein the intermediate member comprises a female socket and the tulip comprises a male end.

8. The system for percutaneous pedicle screw revision procedures of claim 7 wherein the female socket and the male end couple to provide a poly-axial tulip, allowing the tulip to rotate and be orientated in multiple directions.

9. The system for percutaneous pedicle screw revision procedures of claim 1 wherein the first member and the second member are fixed in position.

10. The system for percutaneous pedicle screw revision procedures of claim 1 wherein the first member and the second member are rotatably connected.

* * * * *